US006428822B1

(12) United States Patent
Shi et al.

(10) Patent No.: US 6,428,822 B1
(45) Date of Patent: Aug. 6, 2002

(54) EXTRACTS OF MIXED ARCTIUM LAPPA L., CARROT AND WHOLE RADISH FOR TREATING HYPERTENSION, CONSTIPATION AND DETOXIFICATION

(75) Inventors: Yuan Shi, Little Neck, NY (US); Yongsen Yang; Dong Xu, both of Jiangxi (CN)

(73) Assignee: Chengzhi Life Science Company, Ltd., Beijing (CN)

( * ) Notice: Subject to any disclaimer, the term of this patent is extended or adjusted under 35 U.S.C. 154(b) by 0 days.

(21) Appl. No.: 09/824,925

(22) Filed: Apr. 3, 2001

(51) Int. Cl.$^7$ ................................................. A61K 35/78

(52) U.S. Cl. ...................... 424/764; 424/755; 424/773; 424/777; 424/779; 424/725

(58) Field of Search ................................ 424/725, 755, 424/779, 777, 773

(56) References Cited

U.S. PATENT DOCUMENTS

| | | | |
|---|---|---|---|
| 4,439,458 A | * | 3/1984 | Puri |
| 4,513,009 A | | 4/1985 | Roques |
| 4,559,340 A | | 12/1985 | Neustadt |
| 4,929,641 A | | 5/1990 | Haslanger |
| 4,981,699 A | * | 1/1991 | Inada et al. |
| 5,418,220 A | | 5/1995 | Schmidt |
| 5,736,144 A | * | 4/1998 | Gideon |
| 5,942,233 A | | 8/1999 | Chang |
| 5,948,824 A | | 9/1999 | Salkin |
| 6,096,759 A | | 8/2000 | Wilcox |
| 6,110,951 A | | 8/2000 | Pershadsingh |
| 6,132,794 A | | 10/2000 | Sinha |
| 6,201,014 B1 | | 3/2001 | Gardiner |

FOREIGN PATENT DOCUMENTS

| | | | | |
|---|---|---|---|---|
| CN | 1077741 A1 | * | 10/1993 | |
| CN | 1096932 A | * | 1/1995 | |
| CN | 1252955 A | * | 5/2000 | |
| JP | 63304001 A | * | 12/1988 | |
| JP | 09087191 A | * | 3/1997 | |
| JP | 09004756 | * | 7/1998 | |
| RU | 2095371 C1 | * | 11/1997 | |
| SU | 1625871 A | * | 2/1991 | |
| WO | WO 9907240 A1 | * | 2/1999 | |

OTHER PUBLICATIONS

Peirce, Practical Guide to Natural Medicine, 1999, Stonesong Press Book, William Morrow and Co, Inc.*
Null et al., "Detoxification Therapies", Publisher: Seven Stories Press, 2000, Innerself.com.*
Traditional Herbalism, 2000, www. vitalityworks.com/Productinfo/B/Burdock.htm.*
pp41 and pp42 of the "Chinese Herbal Medicine–Materia Medica", compiled and translated by Dan Bensky and Andrew Gamble with Ted Kaptchuk. (1993) [Exhibit C].

* cited by examiner

Primary Examiner—Leon B. Lankford, Jr.
Assistant Examiner—Ruth A. Davis
(74) Attorney, Agent, or Firm—Albert Wai-Kit Chan; Mark Elkins

(57) ABSTRACT

A mixed substance for treating hypertension, constipation, detoxification, boost immune system produced by extracting arctium lappa L., carrot, and whole radish with water one or two hours at temperature 70° C. 100° C. under agitating, separated the extracts and solid by-products, vacuum condensed the extracts, then at low temperature lyophilized condensed extracts to powder, encapsulated powder or pressed powder to tablet. Patient taking a daily dosage of this vegetable medicine have shown greatly improved healthy condition.

5 Claims, 5 Drawing Sheets

Figure 1:
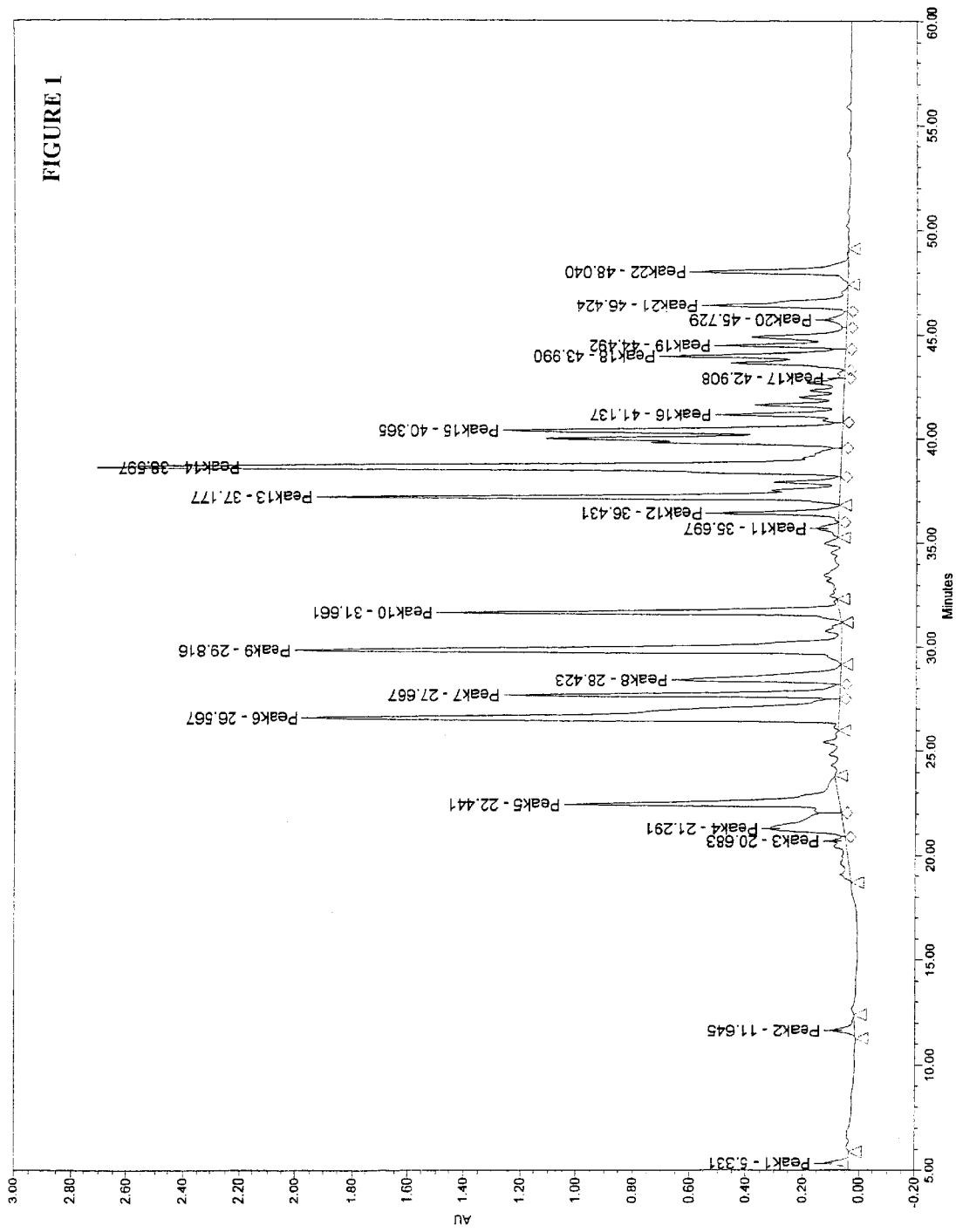

EXTRACTS OF MIXED ARCTIUM LAPPA L., CARROT AND WHOLE RADISH FOR TREATING HYPERTENSION, CONSTIPATION AND DETOXIFICATION

BACKGROUND—FIELD OF INVENTION

This invention relates to vegetable medicine, specifically to cure sickness and improve healthy condition.

BACKGROUND OF THE INVENTION

This invention relates to extracts of arctium lappa L., carrot and whole radish (radish and radish leaves) substance having anti hypertension, detoxification and treating constipation properties. Hypertension is the medical term for high blood pressure. It is defined in an adult as a blood pressure greater than or equal to 140 mmHg systolic pressure or greater than or equal to 90 mmHg diastolic pressure. Blood pressure is measured in millimeters of mercury (mmHg). High blood pressure directly increases the risk of coronary heart disease (which leads to heart attack) and stroke, especially along with other risk factors. High blood pressure can occur in children or adults, but it's more common among people over age 35. Medical science does not understand why most cases of high blood pressure occur, it's hard to say how to prevent it.

Current pharmaceutical treatments for essential hypertension include diuretics, beta-blockers, ACE inhibitors, angaotensin converting enzyme inhibitors, thiazid and calcium antagonists. Some of them were patented, such as U.S. Pat. Nos. 4,559,340. The patent refers to make an antihypertension agents. There are disclosed benzothiadiazinyl and quinazolinyl substituted carboxylalkyl dipeptides, wherein the benzothiodiazinyl oror quinazolinyl portions are joined to the dipeptide portions by an aminocarbonyl group. Compounds of this patent are used for the treatment of congestive heart failure and glaucoma. In addition, compounds of this patent also have diuretic activity.

U.S. Pat. Nos. 6,110,951: Thiazolidine derivatives for the treatment of hypertension. It refers to second medical use of thiazolidine compounds having anti-diabetic properties. Thiazolidine derivatives is a compounds, which is not only used for the treatment of hypertension but also used for the control of essential hypertension.

U.S. Pat. Nos. 4,929,641. Novel mercapto-acylamino acids useful in the treatment of hypertension and combinations of mercapto-acylamino acids and atrial natriuretic factors or angiotensin coverting enzyme inhibitors useful for treating hypertension are disclosed, described mercapto-acylamino acids in the treatment of hypertension and combinations mercapto-acylamino acids and atrial natriuretic factors or angiotensin converting enzyme inhibitors for treating hypertension.

U.S. Pat. Nos. 4,513,009: Aminoacid derivatives and their therapeutic applications. The invention relates to aminoacid derivatives, and compositions containing the same and having enkephalinase-inhibiting, antalgic, antidiarrhea and hypertension activities.

U.S. Pat. Nos. 6,096,759: relates to the treatment of essential hypertension by administration of anti-hypertensive effective of 4-hydroxy-2,2,6,6-tetramethyl-1-piperidine-1-oxyl (tempol).

Currently available anti-hypertensive agents are not without side effects such as the elevation of blood lipids and glucose. The elevation of blood lipids and glucose by these agents has been suggested as a reason why anti-hypertensive agents have not demonstrated any benefits to patients being monitored in death rate studies.

Toxin undermine our health, defines a toxin simply as any substance that creates irritating and/or harmful effects in the body, undermining our health or stressing our biochemical or organ functions. More specifically, a body overloaded with toxin can results in a number of symptoms. These include constipation, stomach bloat, poor digestion, gas, fatigue, weight gain, excessive mucus, poor concentration, headache, poor skin, poor memory, depression, body odor, and bad breath. Some health practitioners relate toxins specific diseases. R. A. Buist, M.D., (International Clinical Nutrition; 1998;8:4) states that chronic fatigue syndrome may be related to toxin exposure. Multiple chemical sensitivity and fibromyalgia (muscle and joint pain) may also be environment-related diseases.

Constipation is a symptom that refers to infrequent bowel movements, but it may also refer to a decrease in the volume or weight of stool, the need to strain to have a movement, a sense of incomplete evacuation, or the need for enemas, suppositories or laxatives in order to maintain regularity.

More serious causes of constipation include growths or areas of narrowing in the colon, so it is wise to seek the advice of a colon and rectal surgeon when constipation persists. Constipation may rarely be a symptom of scieroderma, lupus, or disorders of the nervous or endocrine systems, including thyroid disease, multiple sclerosis, Parkinson's disease, stroke, and spinal cord injuries.

Many medications, including pain killers, antidepressants, tranquilizers, and other chiatric medications, blood pressure medication, diuretics, iron supplements, calcium supplements, and aluminum containing antacides can cause or worsen constipation.

The vast majority of patients with constipation are treated by adding high fiber foods like bran, shredded wheat, whole grain breads and certain fruits and vegetables to the diet, along with increased fluids.

In the U.S. Pat. Nos. 5,948,824: Use a chemical agent of organic origin for reducing or eliminating in waistline or for reducing or eliminating constipation. U.S. Pat. Nos. 5,418,220: Invented to use of dimethicone as an agent for treating constipation.

This invention relates to use mixed vegetables to anti-hypertension detoxification and treating constipation that practiced holistically. It is intent to heal the entire body, instead of just treating the symptoms. Those vegetables contain many nature compounds that play off one another, producing a wide variety of results. Even medical science does not always understand how the compounds work together, or even exactly what they all are.

The invention relates to the novel method of producing a mixed vegetables medicine. The medicine includes arctium lappa L., carrot and whole radish. When extracting arctium lappa L., carrot and whole radish, the extracts have powerful functions such as anti-hypertension, detoxification, and treating constipation.

SUMMARY OF TILE INVENTION

It is an object of the invention to provide a method of producing a medicinal substance for anti-hypertension, detoxification, cure constipation. It has been discovered that arctium lappa L., carrot and whole radish extracts are active as anti-hypertension agent, anti-constipation agent and detoxification agent.

Carrot: Scientific Name: Garden carrot: Daucus carota
Common Name: Wild carrot: daucus, Queen Anne' lace.

Carrot is rich fiber and nutrient content, contemporary herbalists add that it can also be used to promote healthy eyes, soothe indigestion, lower cholesterol, and help prevent cancer. In parts of the Europe today, people sip brews made from the root or dried above ground parts of wild carrot to promote urination (as a mild diuretic, or "water"), prevent worms, and break up bladder stones. The seeds have been used in traditional medicine as a diuretic and to stimulate menstruation, and relieve gas. In years past it was enlisted as a treatment for such wide ranging ailments as worms, diabetes, and kidney disease, and was even considered an aphrodisiac.

Few sources dispute the nutritional richness of the edible carrot (and the root oil), which contains plentiful stores of beta-carotene, a plant form of vitamin A that the body relies on in many important ways. Many of the claims for carrot appear to be based on the presence of vitamin A, including its cancer-preventing potential. Most medicinal claims for carrots demand more research. Investigators are following several interesting leads, however. According to reports, carrot extracts dilate vessels and relax smooth muscles of animal organs isolated in the laboratory, slow heart activity in frog and dog hearts, and lower blood pressure by relaxing the heart smooth muscle in rats. The implications for treating liver, heart, or other diseases in humans still require extensive research. According to a 1995 study, an extract of the carrot may merit investigation as liver protectant, in mice it helped to shield the organ from carbon tetrachloride poisoning.

Evidence indicates that the carrot and the carrot oils are safe to consume in moderation. Too much of either may be unwise, however. Carrot seeds contain a psychoactive agent called myristicin, which, if taken in large amounts, raises the risk for neurologic reactions, skin irritation and blisters can develop after handing the leaves, especially if they are wet and you are then exposed to the sun.

Arctium lappa L.: Pharmaceutical name is fructus arctii lappae. Botanical name: Arctium lappa L.English mane is great burdock fruit, arctium. Pharmacological and clinical research have shown significant in vitro inhibitory effect against streptococcus pneumoniae and many pathogenic fungi. Endocrine effect: ingredients taken from arctium lappa L. showed a significant and prolonged hypoglycemic effect in rats. Action and indication: arctium lappa L. benefits the throat with such symptoms as fever, cough, and sore, red, swollen throat, clears heat and relieves toxicity.

Am J Chin Med 1996, 24(2): 127–37: Described the effects of Arctium lappa L. on anti-inflammatory and free radical scavenger activity were investigated. Subcutaneous administration of A. lappa crude extract significantly decreased carrageenan-induced rat paw edema. When simultaneously treated with CC14, it produced pronounced activities against CC14-induced acute liver damage. The free radical scavenging activity of its crude extract was also examined by means of an electron spin resonance (ESR) spectrometer. The IC50 of A. lappa extract on superoxide and hydroxyl radical scavenger activity was 2.06 mg/ml and 11.8 mg/ml, respectively. These finding suggest that Arctium lappa possess carrageenan induced paw edema and CC14-indeced hepatotoxicity could be due to the scavenging effect of A. lappa.

Chem Pharm Bull (Tokyo) 1996 Dec; 44(12): 2300–4 reported the differentiation inducing activities of lignoids from Arctium lappa L. against mouse myeloid leukemia cells (M1).

Radish: Botanical Name: *Raphanus sativus*, family: N.O.Cruciferae.

DETAILED DESCRIPTION OF THE INVENTION

Methods

The amount of the mixed vegetable composition administered depends upon the percent of active ingredients within its formula, such as arctium lappa L., carrot and whole radish (radish and radish leaves).

Formula1

A tablet composition for oral administration is prepared by combining the following ingredients:

| Ingredient | % W/W |
| --- | --- |
| Arctium lappa L. | 40 |
| Carrot | 60 |

Clean arctium lappa L. and carrot, chopped to small dices or any shape (use chopping processor), poured small dices into a batch container equipped with an agitator and heating jacket, purified water added to the batch container, the amount of purified water was two times of total ingredients amount. Turned on agitator and heated temperature between 70° C.–100° C., Extracting one to two hours, after extracting, separated liquid product and solid by-product, vacuum condensed extracted liquid at temperature not exceeded 100° C., and at low temperature lyophilized condensed extracts to powder, the final step was encapsulated powder or pressed powder to tablet.

The HPLC (high performance liquid chromatography) fingerprints of FORMUL1 extracts (FIG. 1).

C18 column, 300A, 5 uM, 4.6 mmID×250 mmL, Flow rate 1 mL/min, solvent A: 0.1% TFA/Water, solvent B: 0.1% TFA/Acetonitrile. 0–10 min 100% solvent A, 10–70 min 0%–50% solvent B, 70–100 min 50%–100% solvent B, 100–10 min 100%–0% solvent B.

Each tablet contain 500 mg, administration one or two tablet each time, two times a day to a person in need of treatment provides improved condition.

Formula2

| Ingredient | % W/W |
| --- | --- |
| Arctium lappa L. | 20 |
| Carrot | 40 |
| Whole radish | 40 |

Clean arctium lappa L.,carrot and whole radish, chopped to small dices or any shape (use chopping processor), poured small dices into a batch container equipped with an agitator and heating jacket, purified water added to the batch container, the amount of purified water was two times of total ingredients amount. Turned on agitator and heated temperature between 70° C.–100° C., extracting one to two hours, after extracting, separated liquid product and solid by-product, vacuum condensed extracted liquid at temperature not exceeded 100° C., and at low temperature lyophilized condensed extracts to powder, the final step was encapsulated powder or pressed powder to tablet.

Figure 2:
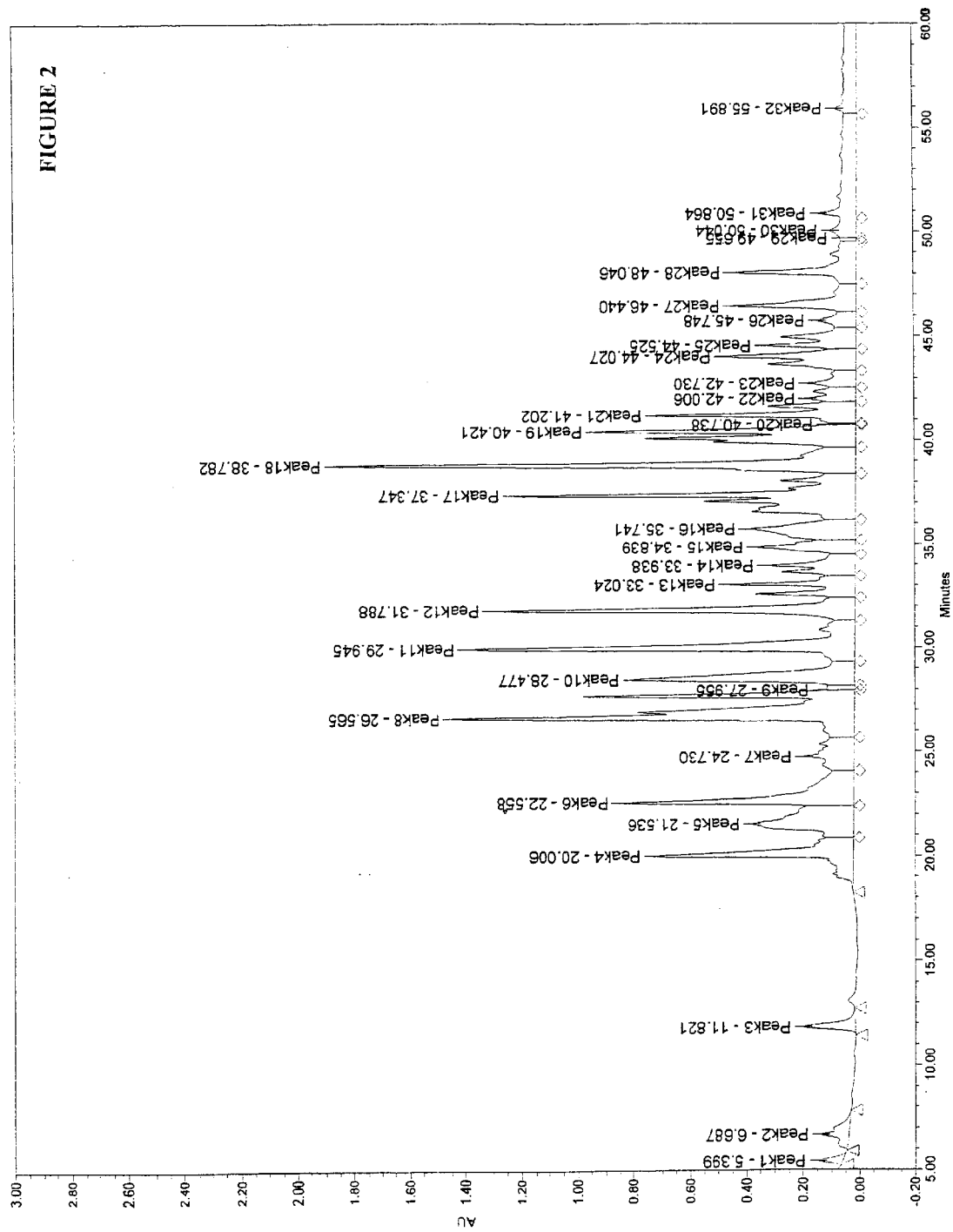

The HPLC (high performance liquid chromatography) fingerprints of FORMUL 2 extracts (FIG. 2).

C18 column, 300A, 5 uM, 4.6 mmID×250 mmL, Flow rate 1 mL/min, solvent A: 0.1% TFA/Water, solvent B: 0.1% TFA/Acetonitrile. 0–10 min 100% solvent A, 10–70 min 0%–50% solvent B, 70–100 min 50%–100% solvent B, 100–110 min 100%–0% solvent B.

FORMULA 2 extracts toxicity study according to <<Procedures and Methods for Toxicological Assessment on Food Safety>> showed none-toxicity.

Conclusion is the extracts of arctium lappa L., carrot and whole radish (radish and radish leaves) according to HPLC fingerprints like FIG. 1 and FIG. 2., then the extracts have drug function that are anti-hypertension, detoxification and cure constipation.

Since the active ingredients derived from vegetables can vary from source to source, the individual components quality control required.

Figure 3:
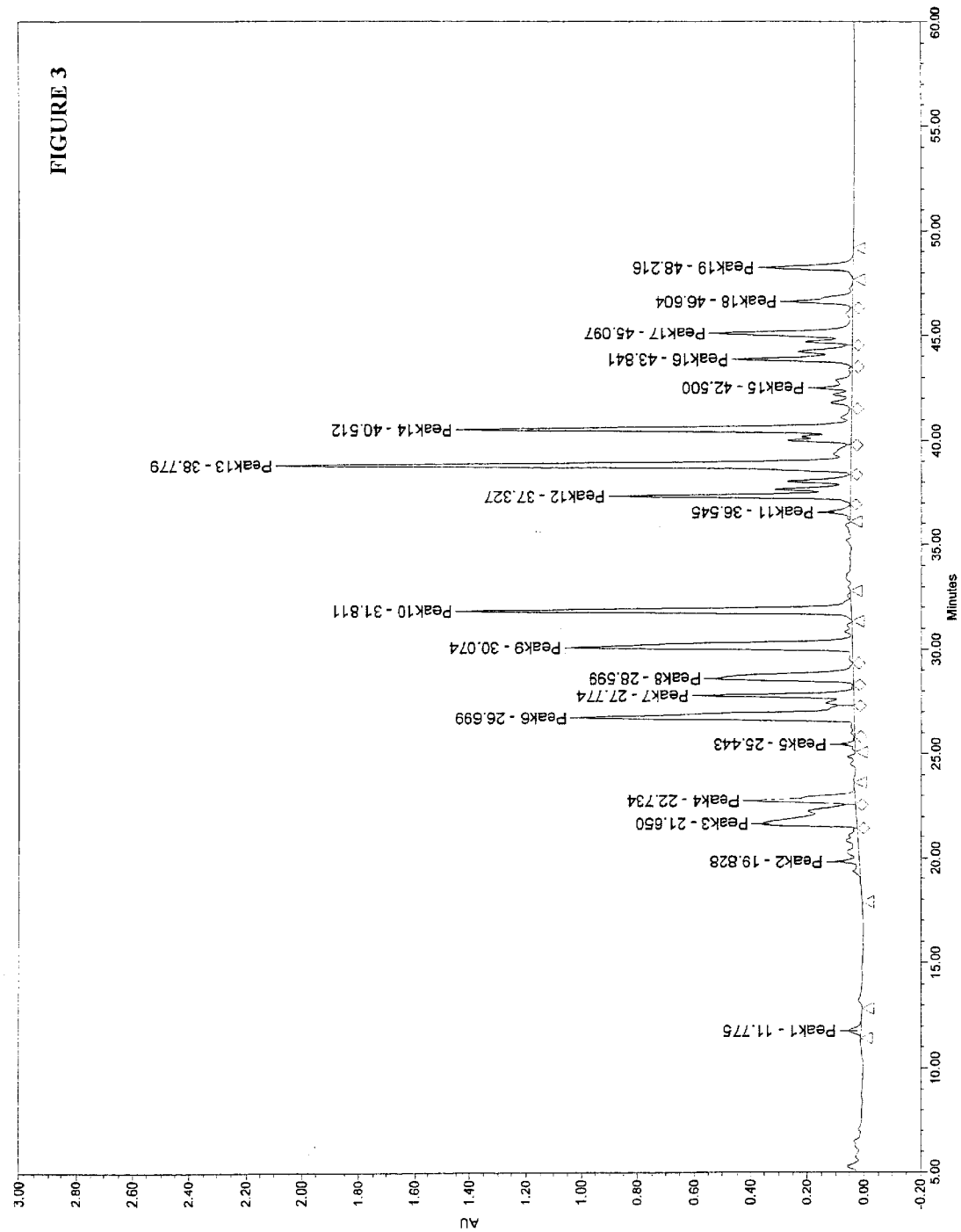

The following standard HPLC fingerprint of extracts of Arctium lappa L. FIG. 3.

Figure 4:
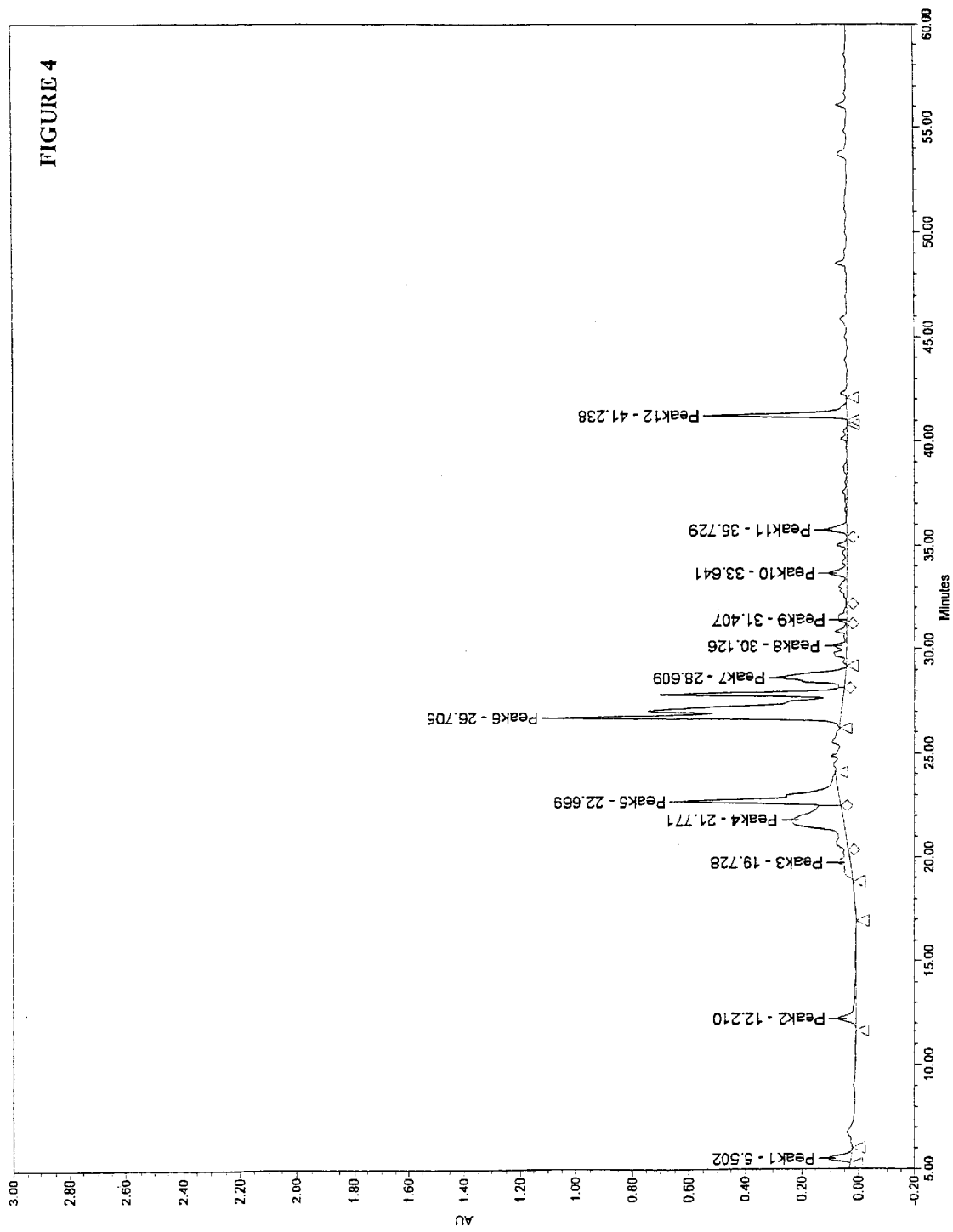

Carrot FIG. 4.

Figure 5:
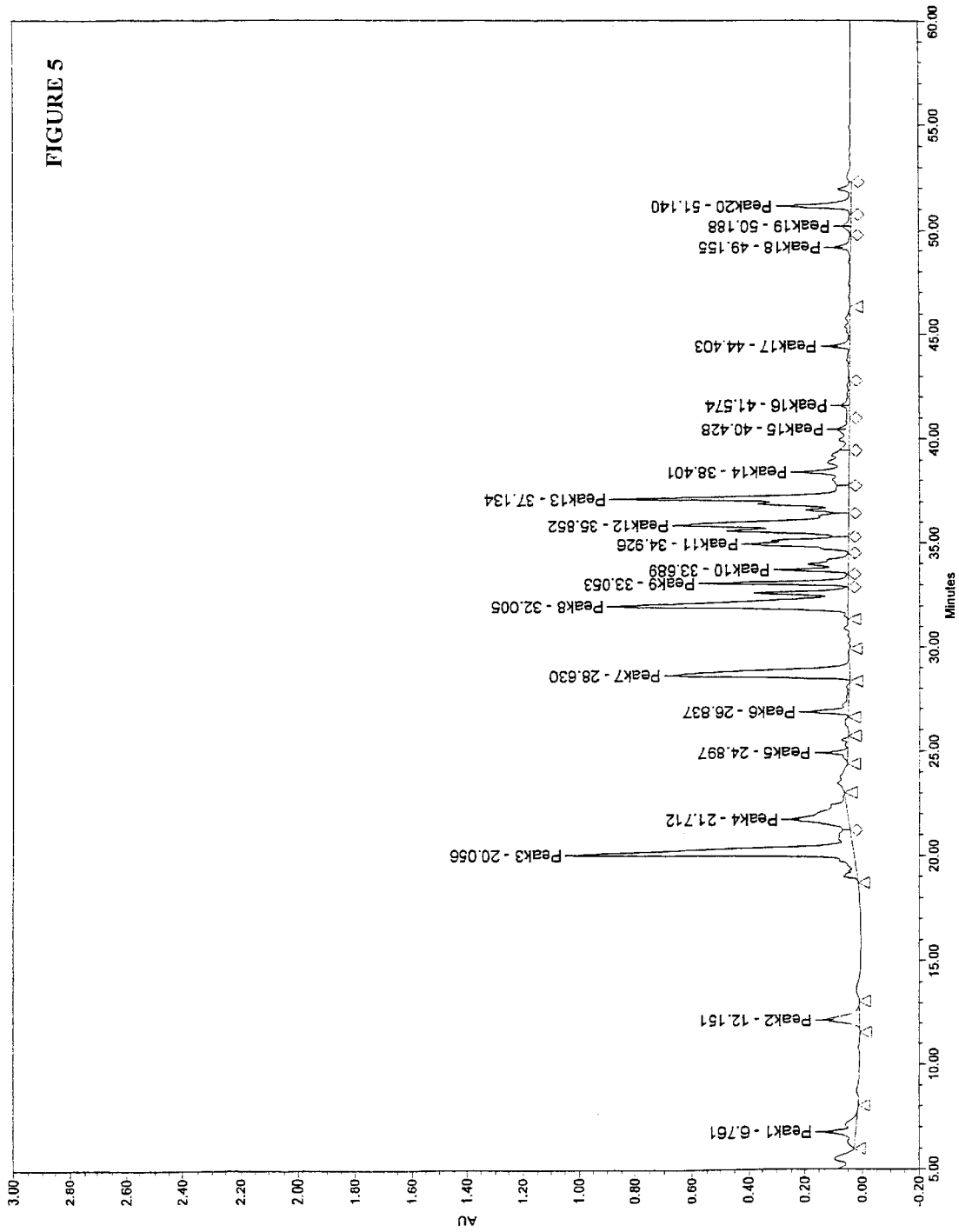

Radish and radish leaves FIG. 5.

C18 column, 300A, 5 uM, 4.6 mmID×250 mmL, Flow rate 1 mL/min, solvent A: 0.1% TFA/Water, solvent B: 0.1% TFA/Acetonitrile. 0–10 min 100% solvent A, 10–70 min 0%–50% solvent B, 70–100 min 50%–100% solvent B, 100–110 min 100%–0% solvent B. As quality control to raw material.

Each tablet contain 500 mg, administration one or two tablet each time, two times a day to a person in need of treatment provides improved condition.

The mixed vegetable tablet of this invention are useful in view of their pharmacological properties. In particular, it is an active anti-hypertensive agents, as evidenced by its ability to reduce blood pressure in mammals in which the blood pressure has become abnormally elevated. The mixed vegetable tablet of this invention also shown activity as detoxification, and anti-constipation agents.

The following examples used formula2.

EXAMPLE1

A 65 years old female has had hypertension history more than ten years, she's blood pressure around 140–165, after she took two tablets each time twice day of mixed vegetable tablets, her blood pressure from 156 to 129 and 88 to 73, continuing ingested same amount of tablet 3 days, blood pressure kept steady around 129 and 73.

EXAMPLE2

An age 43 male has hypertension, he was medication since he had symptom. He stopped medication and ingested mixed vegetable tablet, two times a day, the low blood pressure from 110 to 90, he toke two tablet twice a day for ten days, the reading keep at 90.

EXAMPLE3

A 49 years old male has constipation problem, after used mixed vegetable tablet, started normal bowel movement.

EXAMPLE4

A 44 years old male ingested mixed vegetable tablet, two tablets each time and twice a day, increased bowel movement and urinary. This is a demonstration of detoxification successfully.

CONCLUSION, RAMIFICATIONS, AND SCOPE

Thus the reader will see that mixed vegetable tablet of this invention is a unique medicine. It is simple to use and safe without any side effect. It is a good dietary supplement for adults and seniors. The mixed vegetable medicine can be any shape, size and color are subject to possible substitution.

That is claimed is:

1. A composition comprising extracts of articum lappa L., carrot and whole radish, in a ratio of 20:40:40 percent by weight, wherein the extracts are obtained by extraction in water at about 70° C.–100° C. for about 1–2 hours and has a high pressure liquid chromatography fingerprint as shown in FIG. 2.

2. The composition of claim 1 for detoxification in a human, alleviating constipation or treating hypertension.

3. A method for detoxifying a human comprising administering an effective amount of a composition comprising extracts of articum lappa L., carrot and whole radish, in a ratio of 20:40:40 percent by weight, wherein the extracts are obtained by extraction in water at about 70° C.–100° C. for about 1–2 hours and has a high pressure liquid chromatography fingerprint as shown in FIG. 2.

4. A method for alleviating constipation comprising administering an effective amount of a composition comprising extracts of articum lappa L., carrot and whole radish, in a ratio of 20:40:40 percent by weight, wherein the extracts are obtained by extraction in water at about 70° C.–100° C. for about 1–2 hours and has a high pressure liquid chromatography fingerprint as shown in FIG. 2.

5. A method for treating hypertension comprising administering an effective amount of a composition comprising extracts of articum lappa L., carrot and whole radish, in a ratio of 20:40:40 percent by weight, wherein the extracts are obtained by extraction in water at about 70° C.–100° C. for about 1–2 hours and has a high pressure liquid chromatography fingerprint as shown in FIG. 2.

\* \* \* \* \*